United States Patent [19]
Kitagawa

[11] 4,214,048
[45] Jul. 22, 1980

[54] REAGENT SUITABLE FOR ENZYME IMMUNO ASSAY

[75] Inventor: Tsunehiro Kitagawa, Nagasaki, Japan

[73] Assignee: Dainippon Pharmaceutical Co., Ltd., Osaka, Japan

[21] Appl. No.: 900,167

[22] Filed: Apr. 26, 1978

Related U.S. Application Data

[62] Division of Ser. No. 748,135, Dec. 6, 1976, Pat. No. 4,150,033.

[30] Foreign Application Priority Data

Dec. 12, 1975 [JP] Japan .............................. 50-148787

[51] Int. Cl.² .......................... C12Q 1/66; C12N 9/96
[52] U.S. Cl. .................. 435/7; 260/112 R; 424/12
[58] Field of Search ............. 195/63, 68, 99, 103.5 H; 260/112 R; 424/88, 12; 435/7, 188, 810

[56] References Cited

U.S. PATENT DOCUMENTS

| | | | |
|---|---|---|---|
| 3,770,820 | 11/1973 | Ackerman et al. .................. | 424/5 X |
| 3,852,157 | 12/1974 | Rubenstein et al. .................. | 195/63 |
| 3,875,011 | 4/1975 | Rubenstein et al. .................. | 195/63 |
| 3,887,582 | 6/1975 | Holub et al. ........................ | 526/259 |
| 3,969,287 | 7/1976 | Jaworek et al. .................... | 195/63 X |

OTHER PUBLICATIONS

Barakat et al., *Chem. Abstracts*, vol. 52, (1958), Abs. No. 9025a.
Meek et al., *Chem. Abstracts*, vol. 52, (1958), Abs. No. 8985h.
Wisdom, "Enzyme-Immunoassay", *Clin. Chem.*, vol. 22, No. 8, (1976), pp. 1243-1255.

*Primary Examiner*—Thomas G. Wiseman
*Attorney, Agent, or Firm*—Stevens, Davis, Miller & Mosher

[57] ABSTRACT

A novel maleimidobenzoic acid N-hydroxysuccinimide ester of the formula:

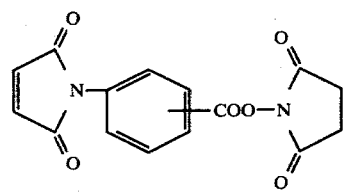

which is suitable as a binding agent for binding an enzyme and an antigen to give an enzyme-labeled antigen of the formula:

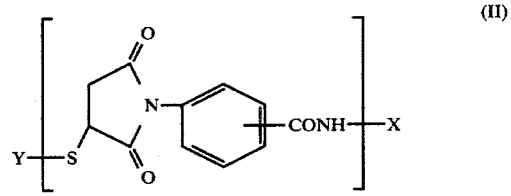

wherein X and Y are different and are each an enzyme or an antigen, and an enzyme immuno assay using the enzyme-labeled antigen (II) and further a kit for the enzyme immuno assay which contains the enzyme-labeled antigen (II).

18 Claims, 4 Drawing Figures

REAGENT SUITABLE FOR ENZYME IMMUNO ASSAY

This is a division of application Ser. No. 748,135, filed Dec. 6, 1976, now U.S. Pat. No. 4,150,033.

The present invention relates to a reagent suitable for an enzyme immuno assay. More particularly, it relates to a novel maleimidobenzoic acid N-hydroxysuccinimide ester (hereinafter, referred to as "MBS") of the formula:

(I)

which is suitable as a binding agent for binding an enzyme and an antigen. Furthermore, it relates to an enzyme-labeled antigen of the formula:

(II)

wherein
X and Y are different and are each an enzyme or an antigen,
and an enzyme immuno assay using the above enzyme-labeled antigen and further a kit containing the enzyme-labeled antigen.

In the present specification, the enzyme immuno assay means all assays wherein an enzyme-labeled antigen is used for the antigen-antibody reaction.

The enzyme immuno assay is generally carried out by subjecting an enzyme-labeled antigen, an unlabeled antigen (i.e. the substance to be measured) and an antibody to a competitive antigen-antibody reaction in a buffer solution, separating the enzyme-labeled antigen bound to the antibody and the free enzyme-labeled antigen (i.e. the enzyme-labeled antigen to which no antibody was bound), and the amount of the unlabeled antigen (i.e. the substance to be measured) being determined from the enzyme activity on either the antibody-bound enzyme-labeled antigen or the free enzyme-labeled antigen. This method has been described in detail in various literatures, for instance, in U.S. Pat. Nos. 3,654,090, 3,839,153 and 3,850,752.

However, the known enzyme-labeled antigens used for the enzyme immuno assay have some disadvantages. That is, the conventional enzyme-labeled antigens are prepared by binding the enzyme and the antigen with the following non-selective bifunctional binding agents:

These binding agents contain the same two functional groups, and hence, when these reagents are used for binding the enzyme and the antigen, unfavorable products such as antigen-antigen and/or enzyme-enzyme complex are formed in addition to the desired enzyme-antigen complex (i.e. the enzyme-labeled antigen). Accordingly, it is difficult to isolate only the desired enzyme-labeled antigen from the mixture of these three products. Particularly, the presence of the enzyme-enzyme complex causes disturbance in the enzyme immuno assay.

Under the circumstances, the present inventor has extensively studied to find an improved binding agent which can selectively bind the enzyme on one hand and the antigen on the other hand. As the result, it has been found that the MBS of the formula (I) can selectively bind the enzyme and the antigen under a very mild condition and further that the enzyme-labeled antigen prepared by case of MBS can favorably be used for the enzyme immuno assay.

An object of the present invention is to provide a novel binding agent suitable for binding an enzyme and an antigen.

Another object of the invention is to provide an improved enzyme-labeled antigen useful for an enzyme immuno assay.

A further object of the invention is to provide an improved enzyme immuno assay using the improved enzyme-labeled antigen.

A still further object of the invention is to provide a kit containing the improved enzyme-labeled antigen useful for an enzyme immuno assay.

These and other objects of the invention will be apparent from the following description.

According to the present invention, the enzyme and the antigen can selectively be bound by using the MBS of the formula (I), and hence, only the desired enzyme-labeled antigen can be prepared. Some compounds structurally similar to the MBS have been described in Helvetica Chimica Acta, Vol. 58, pages 531–541 (1975), but this literature does not describe the application of these compounds to the enzyme immuno assay.

In the present invention, the binding of the enzyme and the antigen consists of the following two steps of (i) reacting an antigen or enzyme, which contains an amino group but does not contain any thiol group, with the ester moiety of MBS to form a bound compound of the formula:

(III)

wherein X is the same as defined above,
and (ii) reacting the resulting bound compound (III) with an enzyme or antigen which contains a thiol group and may optionally contain an amino group, whereby the maleimido moiety of MBS in the bound compound (III) is subjected to the addition reaction with the enzyme or antigen to form the enzyme-labeled antigen of the formula (II).

Thus, MBS is an excellent bifunctional binding agent having a high selectivity and can bind the enzyme and the antigen through two step reactions under a very mild condition, which are substantially different from the binding manner of the conventional binding agents.

The antigen to be bound to the enzyme is usually the same as the substance to be measured and includes a wide range of substances from high molecular substances to low molecular substances (e.g. so-called "haptans").

The antigen use in the first step (i) does not contain any thiol group and contains an amino group or a group convertible into an amino group, wherein the amino group may be contained in the antigen originally or may be chemically introduced. Suitable examples of the antigen which contains originally, an amino group but does not contain any thiol group are hormones such as angiotensin I, insulin, iodothyronines or human chorionic gonadotropin (HCG), compounds having an amino group and a chemical structure partially similar that of the compound to be measured (e.g., α,α'-diphenylpropylamine in case the test compound to be measured is diphenylhydantoin), physiological amines (e.g. serotonin), enzymes other than those used for labeling the antigen, virus specific antigen (e.g. virus hepatitis B), tumor antigen (e.g. α-fetoprotein), immunoglobulins (e.g. IgG, IgE), or the like. Besides, suitable examples of the antigen which does not contain any thiol group and can be introduced with an amino group are haptens, for instance, steroid hormones (e.g. estradiol).

The enzyme used in the first step (i) include all enzymes which contain an amino group but do not contain any thiol group, but preferably, the enzymes satisfy all or some of the following conditions:

(1) It has a high specificity to the substrate.
(2) It is highly stable under assay and storage conditions.
(3) It has a high solubility.
(4) The assay method is simple, sensitive, rapid and cheap.
(5) It is absent from biological fluids.
(6) Its substrates, inhibitors, and disturbing factors are absent from biological fluids.

(7) It retains its activity after chemical treatment for linking antigen.

Suitable examples of these enzymes are peroxidase, glucose oxidase, alkaline phosphatase, or the like.

The enzyme used in the second step (ii) includes all enzymes containing a thiol group and satisfying all or some of the conditions as mentioned above (e.g. β-D-galactosidase) and other enzymes, into which a thiol group is introduced. The introduction of a thiol group into the enzyme may be performed by the method as described, for example, an Archives of Biochemistry and Biophysics, Vol. 96, pages 605–612 (1962).

The antigen used in the second step (ii) may originally contain a thiol group, but if the antigen does not contain any thiol group, it may be chemically introduced thereto. The introduction of a thiol group into the protein or peptide antigen may be performed in the same manner as described above, but when the antigen contains —S—S— bond in the molecule, as in insulin, the thiol group can be produced by reducing the —S—S— bond.

In preferred embodiment of the present invention, an antigen containing an amino group and containing no thiol group is bound to MBS in the first step and then the resultant is bound to an enzyme containing a thiol group in the second step.

In particularly preferred embodiment, a comparatively high molecular antigen (e.g. insulin or angiotensin) is bound to MBS in the first step, and then the resultant is bound to β-D-galactosidase which originally contains a thiol group.

In the most preferred embodiment, among the three position isomers of the compounds of the formula (I), i.e. ortho-substituted compound (hereinafter, referred to as "o-MBS"), meta-substituted compound (hereinafter, referred to as "m-MBS") and para-substituted compound (hereinafter, referred to as "p-MBS"), m-MBS having both excellent stability and excellent reactivity for the amino group is used, and a comparatively high molecular antigen (e.g. insulin or angiotensin) is first bound to the m-MBS, and then the resultant is bound to β-D-galactosidase which originally contains a thiol group.

The reaction in the first and second steps may be carried out by contacting the components each other in a buffer (pH: 6–8) at 10° to 40° C., preferably, 20° to 30° C., for 10 to 180 minutes, occasionally with stirring. This reaction is preferably carried out in the presence of a small amount of a water-soluble organic solvent (e.g. tetrahydrofuran, dioxane, acetone, ethanol), except that the component, such as an enzyme, is inactivated or denatured with the organic solvent. The reaction product thus obtained can be easily purified by conventional methods, such as washing with a buffering solution, column chromatography on a Sephadex (made by Pharmacia Fine Chemicals in Sweden), filtration through a membrane (e.g. Diaflo: a trade name of Amicon Corp. in U.S.A.), or the like.

The ratio of the enzyme to the antigen in the enzyme-labeled antigen of the formula (II) thus obtained may be variable depending on the kinds of the enzyme or the antigen, particularly, on the number of the amino or thiol group contained in the enzyme or antigen.

The MBS of the formula (I) is a novel compound and may be easily prepared by reacting a maleimidobenzoic acid of the formula:

with N-hydroxysuccinimide of the formula:

in an organic solvent (e.g. tetrahydrofuran, dioxane, benzene, acetone) in the presence of a dehydrating agent (e.g. dicyclohexylcarbodiimide) at room temperature for 2 to 3 hours.

The antibody against the enzyme-labeled antigen may be prepared by immunizing an appropriate animal, such as rabbit, horse, goat, guinea pig or cattle with the corresponding antigen containing an adjuvant to produce an antibody in the serum. The antibody-containing serum thus obtained may be used for the enzyme immuno assay as it is (i.e. without purification) or after purification. Besides, the antibody (antiserum) against haptens may be prepared by absorbing or binding the haptens to a high molecular substance (e.g. albumin) and then immunizing an animal with the resultant together with an adjuvant likewise.

The enzyme immuno assay using the present enzyme-labeled antigen may be carried out in the same manner as described in various literatures, for instance, in U.S. Pat. Nos. 3,654,090, 3,850,752 and 3,839,153, that is, by subjecting to the competitive immunoreaction between the enzyme-labeled antigen and an unlabeled antigen (i.e. a substance to be measured) for the antibody in a buffer solution; separating the resulting enzyme-labeled antigen-antibody complex by centrifugation, or adding the second antibody to the above reaction mixture to precipitate the enzyme-labeled antigen-antibody complex (so-called "Double Antibody Method"); measuring the activity of the labeled enzyme in the precipitate or in the supernatant fluid by a conventional method; and then calculating the amount of the unlabeled antigen in the sample from the calibration curve obtained by the enzyme immuno assay using a predetermined amount of a standard antigen. The second antibody can be prepared in the same manner as described above, wherein the first antibody (immunoglobulins) is used as the antigen for the production of the second antibody in the serum of an animal who is different from the animal used in the preparation of the first antibody.

Thus, in the enzyme immuno assay using the present enzyme-labeled antigen, the essential reagents are (a) an enzyme-labeled antigen prepared by binding the enzyme and the antigen with MBS, (b) an antibody against the antigen in the above (a), and (c) a substrate of the enzyme in the above (a), and the following reagents are optionally used:

(d) the second antibody, and (e) a reagent for measuring the enzyme activity other than the substrate (c).

The reagents (a), (b) and (d) may be reserved in the form of a buffer solution thereof in a cooled place, but may preferably be reserved in the freeze-dried state, which is redissolved in water or a buffer solution when used. The freeze-dried product can be prepared by freeze-drying a solution thereof, to which are optionally added stabilizers, fillers, or the like. The reservation in the freeze-dried state is preferable in the standpoints of their stability and easiness in handling.

The reagent (e) is specified depending on the kinds of the enzyme in (a) and the method, and it includes a chromogenic reagent, coenzyme, enzyme reaction-stopping reagent, or the like.

The present invention is illustrated by the following Examples, but is not limited thereto.

EXAMPLE 1

Preparation of o-, m- and p-MBS

To a solution of o-, m- or p-maleimidobenzoic acid (217 mg) in tetrahydrofuran (30 ml) are added N-hydroxysuccinimide (130 mg) and dicyclohexylcarbodiimide (224 mg). The mixture is stirred at room temperature for 2 hours, and the precipitated N,N'-dicyclohexylurea is filtered off. The filtrate is concentrated under reduced pressure. The residue thus obtained is purified by silica gel column chromatography (elute: chloroform), and then recrystallized from ether-dichloromethane to give o-, m- or p-MBS having the properties as shown in the following Table 1.

| | Melting point (°C.) | Elementary Analysis $C_{15}H_{10}N_2O_6$ Calculated (%) / Found (%) | | | IR (KBr) $\nu$ max (cm$^{-1}$) | NMR (60MHz . CDCl$_3$) $\delta$-value | | |
|---|---|---|---|---|---|---|---|---|
| | | | | | | —CH$_2$CH$_2$ | —CH=CH— | Hydrogen in benzene ring |
| o-MBS | 125 ~ 128 | C 57.33 57.29 | H 3.21 2.95 | N 8.92 8.85 | 3100 (=C—H), 1770, 1731, 1720 (Maleimide, Succinimide,—COON⟨), 1559, 1495, 1390, 1202, 1065 (—COON⟨), 987, 842, 701 | 2.82(s) 4H | 6.86(s) 2H |  Ha: 7.28–7.95 (m), 3H Hb: 8.13–8.37 (m), 1H |

-continued

| | Melting point (°C.) | Elementary Analysis $C_{15}H_{10}N_2O_6$ Calculated (%) Found (%) | | | I R (KBr) $\nu$ max (cm$^{-1}$) | NMR (60MHz . CDCl$_3$) $\delta$-value | | |
|---|---|---|---|---|---|---|---|---|
| | | | | | | —CH$_2$CH$_2$ | —CH=CH— | Hydrogen in benzene ring |
| m-MBS | 182 ~ 185 | C 57.33 57.22 | H 3.21 2.98 | N 8.92 8.72 | 3110 (=C—H), 1773, 1738, 1712 Maleimide, Succinimide, —COON⟨ ), 1487, 1446, 1392, 1204, 1075 (—COON⟨ ), 830, 699 | 2.90(s) 4H | 6.89(s) 2H |  Ha: 7.57–7.77 (m), 2H Hb: 8.03–8.23 (m), 2H |
| p-MBS | 198 ~ 200 | C 57.33 56.90 | H 3.21 3.18 | N 8.92 8.65 | 3095 (=C—H), 1774, 1740, 1718 (Maleimide, Succinimide,—COON⟨ ), 1605, 1513, 1375, 1208, 1075 (—COON⟨ ), 1002, 832, 699 | 2.90(s) 4H | 6.90(s) 2H |  Ha: 7.65 (d), J = 8.8Hz, 2H Hb: 8.23 (d), J = 8.8Hz, 2H |

R: maleimide

Among two functional groups in these MBS compounds, the maleimido moiety is considered to be unstable, while the ester moiety is considered to be less reactive for the antigen or enzyme. Then, the stability and reactivity of the MBS compounds were tested. The results are shown in the following Table 2 and Table 3, respectively.

Table 2

| | Stability of MBS | | | | |
|---|---|---|---|---|---|
| | Incubation time | | | | |
| Test compound | 30 minutes pH range | | | | 20 minutes |
| | 5.0 | 6.0 | 7.0 | 8.0 | 7.5 |
| o-MBS | 3.1 | 6.2 | 21.4 | 69.0 | 18.8 |
| m-MBS | 2.9 | 2.5 | 7.1 | 43.8 | 9.4 |
| p-MBS | 3.8 | 6.6 | 32.0 | 52.0 | 37.5 |

[Remark]: The numeral in the above table means percentage of decomposed maleimido group of MBS, when a solution of the test compound (10 mmol) in tetrahydrofuran (20 μl) is mixed well with 0.5 ml of a 0.05 M phosphate buffer (pH: 6.0, 7.0, 7.5 or 8.0) or a 0.05 M citrate buffer (pH: 5.0), and the mixture is incubated for 20 or 30 minutes.

Table 3

| | Reactivity of MBS |
|---|---|
| Test compound | Reactant: lysine |
| o-MBS | 32.6 |
| m-MBS | 41.0 |
| p-MBS | 27.5 |

[Remark]: The numeral in the above table means the acylation percentage of the reactant: lysine with MBS, when a solution of the test compound (1 mmol) in tetrahydrofuran (10 μl) is mixed with 0.1 ml of a 0.1 M lysine - 0.05 M phosphate buffer (pH: 7.5) and the mixture is reacted at 30° C. for 20 minutes.

EXAMPLE 2

Measurement of insulin (a) Binding of m-MBS to insulin

To a 0.05 M phosphate buffer (pH: 7.0, 1 ml) containing pig insulin [made by Schwarz Mann G.m.b.H., 6 mg (1 μmol), 25.5 U/mg] is added a solution of m-MBS (1.2 μmol, i.e. 5 mg/ml) in tetrahydrofuran (75 μl), and the mixture is allowed to stand at room temperature for 30 minutes, during which it is occasionally stirred. To the resulting mixture is added a 1 M citrate phosphate buffer (pH: 5.0, 1 ml), and the resulting precipitates are separated by centrifuging (800×g, 15 minutes). The precipitates thus obtained are washed twice with a 0.01 M citrate buffer (pH: 5.3, 2 ml) and dried under reduced pressure to give [m-MBS]-[insulin] bound product (5.5 mg).

(b) Binding of [m-MBS]-[insulin] product to β-D-galactosidase.

To a 0.05 M phosphate buffer (pH: 7.0, 1 ml) containing β-D-galactosidase of Eschrichia coli [made by Boehringer Mannheim G.m.b.H. in West Germany, 0.93 nmol (500 μg)] is added a 0.05 M phosphate buffer (pH: 7.0, 0.15 ml) containing the [m-MBS]-[insulin] bound product (151 μg, i.e. maleimido content: 3.6 nmol) obtained in the above (a), and the mixture is allowed to stand at room temperature for 2 hours.

The resulting mixture is passed through a Sepharose 6B column (1.8×33 cm, made by Pharmacia Fine Chemicals in Sweden), which is eluted with a 0.1 M NaCl—0.02 M phosphate buffer (pH: 7.0), and thereby the desired [β-D-galactosidase]-[m-MBS]-[insulin] product is separated from unreacted free enzyme and [m-MBS]-[insulin] product. Yield: about 80% calculated from the enzymatic activity thereof. The molar ratio of insulin and β-D-galatosidase of the product is about 1:1.8.

(c) Measurement of insulin

Figure 1:
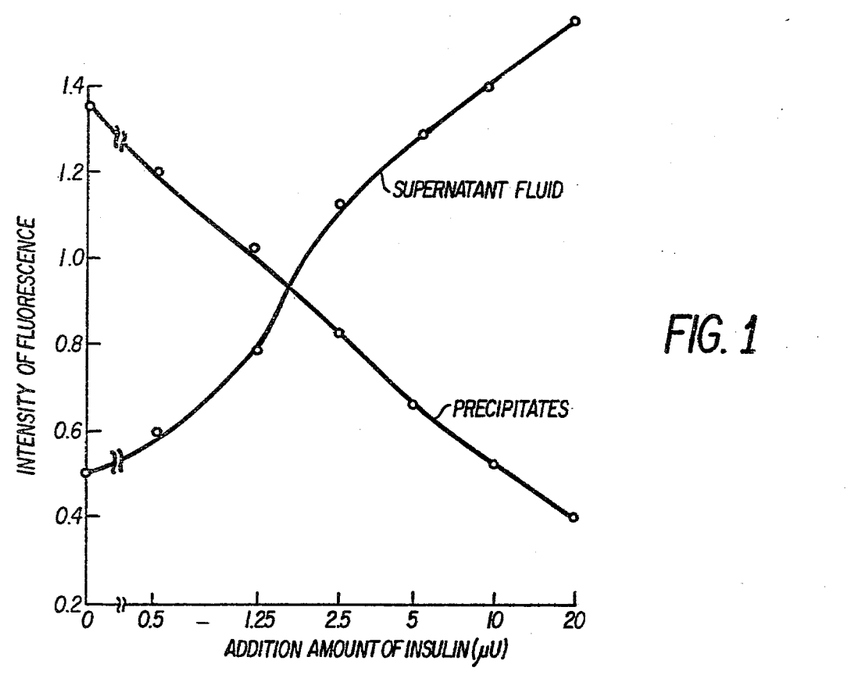

The main fraction of the [β-D-galactosidase]-[m-MBS]-[insulin] bound product (i.e. enzyme-labeled antigen) obtained in the above (b) is diluted 200 times with water. The diluted enzyme-labeled antigen (10 μl) is mixed with a 0.1% rabbit serum albumin—1 mM MgCl$_2$—0.1 M NaCl—0.1% NaN$_3$—0.02 M phosphate buffer (pH: 7.0) (0.2 ml) containing insulin (i.e. unlabeled antigen, 0–20 μU) and anti-pig insulin guinea pig antiserum (made by Dainabot Radioisotope Lab., Ltd. in Japan, 50 μl) (i.e. the first antibody). The mixture is allowed to stand at 4° C. for 16 hours, and thereto is added anti-rabbit 7s-γ-globulin anti-guinea pig serum (i.e. the second antibody, 10 μl). The mixture is further allowed to stand at 4° C. for 8 hours and then subjected to centrifugation (800×g, 15 minutes). The activity of β-D-galactosidase in the supernatant fluid or the precipitates thus obtained is measured by the method as mentioned in the following item (d), from which a standard calibration curve as shown in the accompanying FIG. 1 is drawn. Accordingly, it is clear that the insulin of 0.5 to 20 μU can be measured by this enzyme immuno assay.

(d) Measurement of the activity of β-D-galactosidase

To a solution of a 0.1 mM 4-methylumbellifery-β-D-galactoside—0.02 M sodium phosphate—0.1% rabbit serum albumin—1 mM $MgCl_2$—0.1 M NaCl—0.1% $NaN_3$ (pH: 7.0) (i.e. the substrate solution, 0.15 ml) is added the supernatant fluid (50 μl) obtained after the antigen-antibody reaction in the above (c), and the mixture is kept at 30° C. for 60 minutes.

Alternatively, the precipitates obtained in the above (c) are washed with a 0.05 M phosphate buffer (pH: 7.0, 2 ml) and thereto is added the above substrate solution (0.15 ml), and the mixture is kept at 30° C. for 30 minutes.

To each of the above mixtures is added a 0.1 M glycine—NaOH buffer solution (pH: 10.3, 2.5 ml) in order to stop the reaction. The 4-methylumbelliferone produced in the reaction mixture in proportion to the activity of enzyme-labeled antigen is measured by a MPF 4 type spectrofluorometer (made by Hitachi, Ltd. in Japan) at excitation wave length: 365 nm and emittion wave length: 448 nm.

EXAMPLE 3

Measurement of Angiotensin I (a) Binding of m-MBS to angiotensin I

To a 0.05 M phosphate buffer (pH: 7.0, 1 ml) containing angiotensin I (1.4 μmol, i.e. 2 mg) is added a solution of m-MBS (4.2 μmol, i.e. 5 mg/ml) in tetrahydrofuran (0.26 ml). The mixture is allowed to stand at room temperature for 30 minutes, during which it is occasionally shaken. To the reaction mixture is added a 1 M citrate buffer (pH: 5.0, 0.5 ml), and the mixture is passed through a Sephadex G-15 column (1.9×38 cm, made by Pharmacia Fine Chemicals in Sweden), which is eluted with a 0.02 M citrate—0.1 M NaCl buffer, and thereby the desired [m-MBS]-[angiotensin I] product is separated from the unreacted angiotensin I and m-MBS.

(b) Binding of [m-MBS]-[angiotensin I] product to β-D-galactosidase

To a 0.05 M phosphate buffer (pH: 7.0, 0.5 ml) containing β-D-galactosidase (0.93 nmol, i.e. 500 μg) is added a 0.05 M phosphate buffer (pH: 7.0, 0.5 ml) containing the [m-MBS]-[angiotensin I] product (maleimido content: 2.8 nmol) obtained in the above (a). The mixture is allowed to stand at room temperature for 2 hours. The reaction mixture is passed through a Sephadex G-25 column (1.8×42 cm, made by Pharmacia Fine Chemicals in Sweden), which is eluted with a 0.1 M NaCl—0.02 M phosphate buffer, and thereby a main fraction containing [β-D-galactosidase]-[m-MBS]-[angiotensin I] is obtained.

(c) Measurement of angiotensin I

Figure 2:
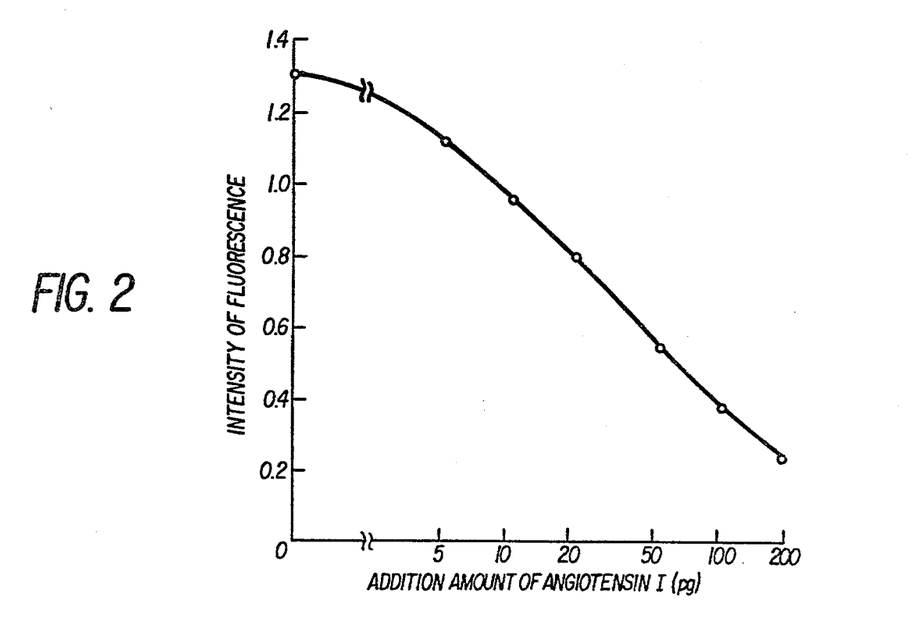

The main fraction containing [β-D-galactosidase]-[m-MBS]-[angiotensin I] (i.e. the enzyme-labeled antigen) obtained in the above b) is diluted 1,000 times with water. The diluted enzyme-labeled antigen (10 μl) is mixed with the same buffer (0.2 ml) used in Example 2, (c) containing angiotensin I [i.e. unlabeled antigen, 0–800 nm (nanogram: $10^{-9}$ g)] and anti-angiotensin I rabbit serum (i.e the first antibody, 50 μl). The mixture is allowed to stand at room temperature for 8 hours, and thereto is added anti-rabbit 7s-γ-globulin goat antiserum (i.e. the second antibody, 10 μl). The mixture is further allowed to stand at 4° C. for 16 hours and then subjected to centrifuging (800×g, 15 minutes). The enzyme activity of the supernatant fluid and the precipitates thus obtained is measured in the same manner as described in Example 2, d), from which a standard calibration curve of angiotensin I for the enzyme immuno assay is drawn as shown in the accompanying FIG. 2. Accordingly, it is clear that the angiotensin of 5 to 100 pg (picogram: $10^{-12}$ g) can be measured by this enzyme immuno assay.

EXAMPLE 4

Measurement of triiodothyronine (hereinafter, referred to as "$T_3$")

(a) Preparation of [$T_3$]-[m-, p- or o-MBS]-[β-D-galactosidase] product

A 0.1 N NaOH aqueous solution (50 μl) containing $T_3$ (made by Sigma Chemical Co. in U.S.A., 0.5 μmol) is mixed with a 0.05 M phosphate buffer (pH: 7.0, 1 ml), and thereto is added dropwise with stirring a solution of m-, p- or o-MBS (0.5 μmol) in tetrahydrofuran (25 μl). The mixture is reacted at room temperature for 10 minutes, and thereto is added a 0.2 M citrate—phosphate buffer (pH: 4.3, 40 μl). The resulting precipitates are separated by centrifuging (800×g, 10 minutes) and is washed with a 0.05 M citrate—phosphate buffer (pH: 4.3, 1 ml) with centrifuging. To the precipitates thus obtained is added a 0.05 M phosphate buffer (pH: 7.0, 1 ml) and thereto is further added with stirring β-D-galactosidase (0.19 nmol, i.e. 100 μg). After the mixture is stirred for 10 minutes, a 0.1 M glycine—NaOH buffer (pH: 10.3, 5 ml) is added thereto. The mixture is filtered through a Diaflo PM 30 (made by Amicon Corp. in U.S.A.), to remove the unreacted [m-, p- or o-MBS]-[$T_3$] product or unreacted $T_3$. The resulting residue is further washed twice with a 0.05 M phosphate buffer (pH: 7.0, 3 ml) and then is added to a 0.05 M phosphate buffer (pH: 7.0, 1 ml) and thereto is further added a 1% bovine serum albumin solution (0.5 ml).

(b) Measurement of $T_3$

Figure 3:
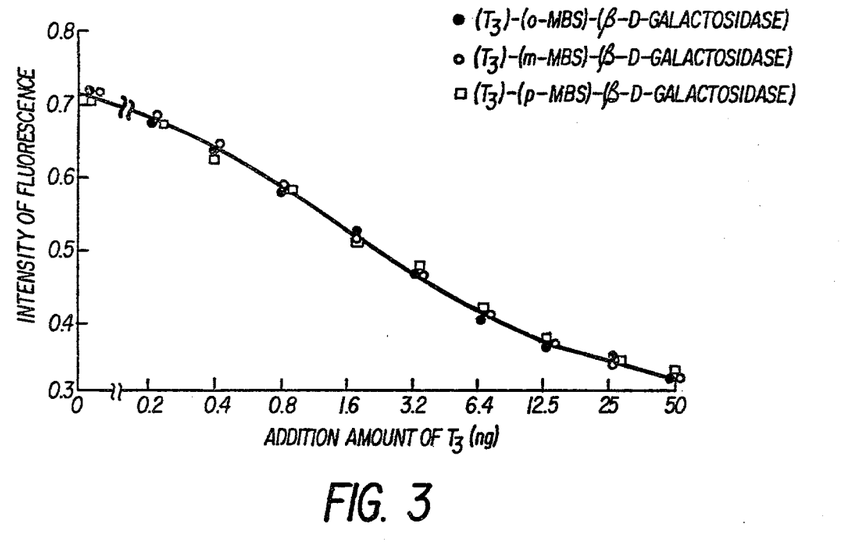

The fraction of [$T_3$]-[m-, p- or o-MBS]-[β-D-galactosidase] (i.e. enzyme-labeled antigen) obtained in the above (a) is diluted 100 times with water. The diluted enzymelabeled antigen (10 μl) is mixed with a 0,02 M Tris-HCl—0.9% NaCl solution (pH: 7.0, 1 ml) containing standard $T_3$ (0–50 ng) and $T_3$ rabbit antiserum (made by Dainippon Pharmaceutical Co., Ltd. in Japan, 50 μl, which is diluted 100 times with water). The mixture is allowed to stand at 5° C. for 5 hours, and thereto is added anti-rabbit IgG goat antiserum (made by Miles Laboratories Inc. in U.S.A., 10 μl). The mixture is allowed to stand at 5° C. for 16 hours and then subjected to centrifuging (800×g, 10 minutes). To the resulting precipitates is added the above buffer (1 ml), and the mixture is further centrifuged. To the precipitates is added a 0.1 mM 4-methylumbelliferyl-β-D-galactoside—0.02 M phosphate buffer (pH: 7.0, 0.15 ml). After the mixture is kept at 30° C. for 30 minutes, the β-D-galactosidase activity thereof is measured in the same manner as described in Example 2, d), from which a calibration curve as shown in the accompanying FIG.

3 is drawn. Accordingly, it is clear that the $T_3$ of 200 pg to 50 ng can be measured by this enzyme immuno assay.

EXAMPLE 5

(a) Preparation of [diphenylpropylamine]-[m-MBS]-[β-D-galactosidase] product To a solution of m-MBS (3,2 μmol, i.e. 1.1 mg/0.16 ml) in tetrahydrofuran is added a solution of 3,3-diphenylpropylamine (3.2 μmol) in ethanol (32 μl). The mixture is stirred at room temperature for 1 hour. The reaction mixture (25 μl) is added with stirring to a 0.05 M phosphate buffer (pH: 7.0) containing β-D-galactosidase (0.19 nmol, i.e. 100 μg). After allowing to stand for 10 minutes, the mixture is filtered through a Diaflo PM 30 (made by Amicon Corp. in U.S.A.). The residue is washed twice with a 0.05 M phosphate buffer (pH: 7.0, 3 ml) and filtered. To the residue thus obtained are added a 0.05 M phosphate buffer (pH: 7.0 1 ml) and a 1% bovine serum albumin (0.5 ml).

(b) Measurement of diphenylhydantoin by enzyme immuno assay

Figure 4:
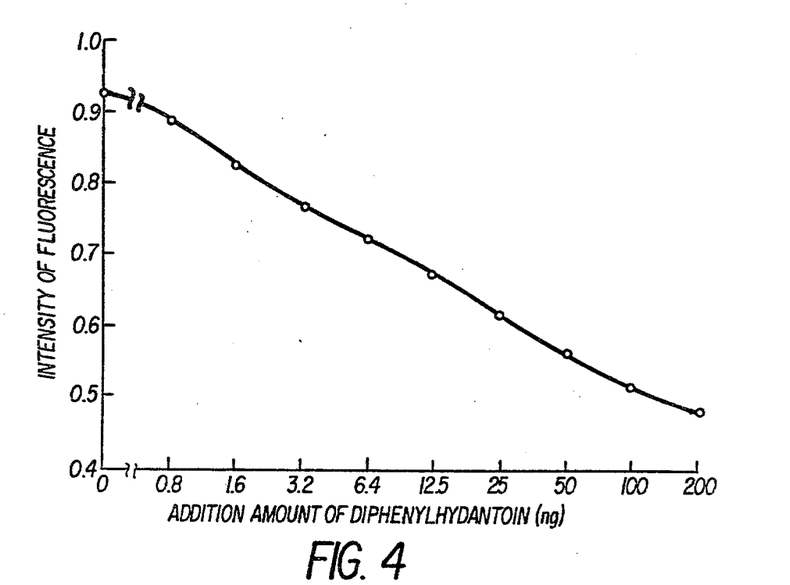
Figure 5:
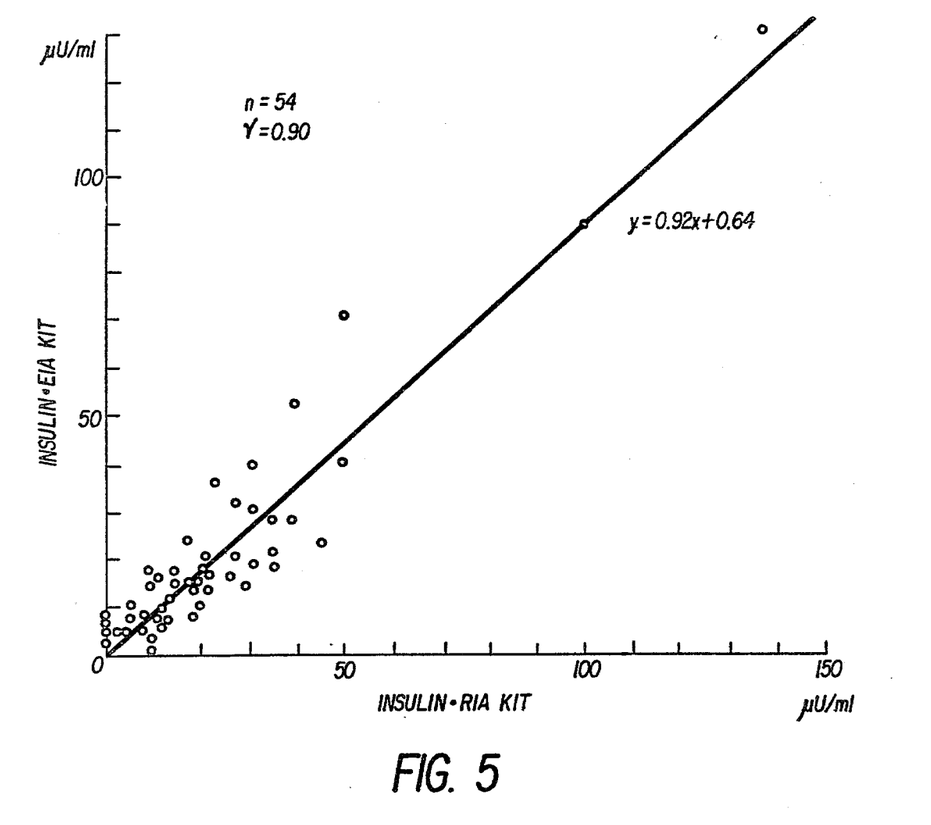

A ten times diluted solution (10 μl) of the [diphenylpropylamine]-[m-MBS]-[β-D-galactosidase] product obtained in the above a), diphenylhydantoin (0–50 ng) and diphenylacetylated bovine albumin rabbit antiserum (made by Dainippon Pharmaceutical Co., Ltd. in Japan, 10 μl, which is diluted 20 times with water) are added to a 0.02 M Tris-HCl—0.9% NaCl (pH: 7.0, 1 ml). The mixture is allowed to stand at 5° C. for 5 hours, and thereto is added anti-rabbit IgG goat antiserum (made by Miles Latoratories Inc. in U.S.A., 10 μl). The mixture is allowed to stand at 5° C. for 16 hours and then subjected to centrifuging (800×g, 10 minutes). The resulting precipitates are washed with the above buffer (1 ml) with centrifuging, and then the ⊖-D-galactosidase activity is measured in the same manner as described in Example 2, d), from which a calibration curve as shown in the accompanying FIG. 4 is drawn. Accordingly, it is clear that the diphenylhydantoin of 0.8 to 100 ng can be measured by this enzyme immuno assay.

EXAMPLE 6

Preparation of a kit suitable for the measurement of insulin

A: Buffer

Bovine serum albumin (60.6 g), NaCl (272.7 g), $Na_2HPO_4.12H_2O$ (149.5 g), $NaH_2PO_4.H_2O$ (29.7 g) and $NaN_3$ (30.3 g) are mixed well. The mixture (each 5,374 mg) is added to 100 bottles of a 15 ml brown bottle. When used, the content of the brown bottle is dissolved in water so as to make 300 ml in final, which is a 0.2% bovine serum albumin—0.9% NaCl—0.1% $NaN_3$—0.02 M phosphate buffer (pH: 7.0) [Reagent A].

B: Enzyme-labeled antigen

To the fraction (0.53 ml) containing the [β-D-galactosidase]-[m-MBS]-[insulin] bound product obtained in Example 2 is added the Reagent A (buffer) so as to make 1,060 ml in final (it is, thereby, diluted 2,000 times). The mixture (each 10.5 ml) is put into 100 brown bottles with 15 ml volume [Reagent B].

C: The First Antibody

To anti-pig insulin guinea pig antiserum [30 μl, containing 37,000 unit of the first antibody, which is prepared in the same manner as described in J. Clin. Invest., Vol. 39, page 1157 (1960)] is added a 0.5% aqueous solution of a normal guinea pig serum (222 ml) (it is, thereby, diluted about 7,400 times). The mixture (each 2.2 ml) is added to 100 brown bottles with 15 ml volume, and then is freeze-dried.

When used, this freeze-dried product is dissolved in a buffer (11.0 ml) to give the first antibody solution having a concentration of 1 unit/0.1 ml [Reagent C].

The term "unit" used above means that one unit is the amount of the antibody which can be combined with 50% of insulin labeled with $^{125}I$, when the antibody is reacted with the $^{125}I$-insulin (100 pg).

D: The Second Antibody

Anti-guinea pig IgG rabbit antiserum [each 2.1 ml, which is prepared in the same manner as described in Biochem. J., Vol. 88, page 137 (1963)] is added to 100 brown bottles with 15 ml volume and is freeze-dried.

When used, the freeze-dried product is dissolved in the Reagent A (buffer, 10.5 ml) [Reagent D]. This solution (0.1 ml) has an activity enough to proceed the antigen-antibody reaction with the Reagent C (the first antibody, 0.1 ml)

E: Standard Insulin

An insulin solution (concentration: 640 μU/ml), each 1.0 ml) is added to 100 brown bottles with 15 ml volume and is freeze-dried.

When used, the freeze-dried product is dissolved in water so as to make 2.0 ml in final, in which 320 μU/ml of insulin is contained. This insulin stock solution is further diluted by two fold dilution method for obtaining a standard insulin calibration curve [Reagent E].

F: Substrate

4-Methylumbelliferyl-β-D-galactoside (63 mg), $Na_2HPO_4.12H_2O$ (8,679 mg), $NaH_2PO_4$ (1,760 mg), bovine serum albumin (1,760 mg), $NaN_3$ (1,760 mg), $MgCl_2$ (352 mg) and NaCl (10.56 g) are mixed well. The mixture (each 227 mg) is added to 100 brown bottles with 20 ml volume. When used, it is dissolved in water so as to make 16.0 ml in final [Reagent F].

G: Buffer

A 1.5 M glycine—NaOH buffer (pH: 10.3, each 20.0 ml) is added to 100 brown bottles with 20 ml volume. When used, it is diluted with water so as to make 300 ml in final [Reagent G].

Thus, there are prepared 100 sets of the kit consisting of each one bottle of the above A to G (hereinafter referred to as "INSULIN EIA KIT"), which are used for 100 assays.

By using this "INSULIN EIA KIT", the enzyme immuno assay of insulin is carried out as follows:

A mixture of Reagent A (buffer, 0.5 ml), Reagent B (enzyme-labeled antigen, 0.1 ml), Reagent C (the first antibody, 0.1 ml) and the test sample or standard insulin solution (an appropriate amount) is incubated at 4° C. for 24 hours. To the mixture is added Reagent D (the second antibody, 0.1 ml), and the mixture is incubated at 4° C. for 8 hours and then subjected to centrifuging (800×g, 15 minutes). The resulting precipitates are washed with Reagent A (buffer, 2.0 ml) with centrifuging, and then the enzyme activity thereof is measured in the same manner as described in Example 2, (d).

What is claimed is:

1. An enzyme-labeled antigen suitable for an enzyme immuno assay having the following formula:

wherein X and Y are different and are each an enzyme or antigen.

2. The enzyme-labeled antigen according to claim 1, which has the following formula:

wherein X and Y are the same as defined in claim 1.

3. The enzyme-labeled antigen according to claim 1, wherein X is an antigen and Y is an enzyme.

4. The enzyme-labeled antigen according to claim 3, wherein X is insulin and Y is β-D-galactosidase.

5. The enzyme-labeled antigen according to claim 3, wherein X is triiodothyronine and Y is β-D-galactosidase.

6. The enzyme-labeled antigen according to claim 3, wherein X is angiotensin I and Y is β-D-galactosidase.

7. The enzyme-labeled antigen according to claim 1, wherein X is an enzyme and Y is an antigen.

8. The enzyme-labeled antigen according to claim 1, wherein one of X and Y is a hormone.

9. The enzyme-labeled antigen according to claim 5, wherein the hormone is a member selected from the group consisting of insulin, angiotensin I and iodothyronines.

10. The enzyme-labeled antigen according to claim 1, wherein one of X and Y is a hapten.

11. The enzyme-labeled antigen according to claim 10, wherein the hapten is diphenylpropylamine.

12. The enzyme-labeled antigen according to claim 1, wherein Y is β-D-galactosidase.

13. The enzyme-labeled antigen according to claim 1, wherein X is a member selected from the group consisting of peroxidase, glucose oxidase and alkaline phosphatase.

14. In a method for conducting an enzyme immuno assay which comprises subjecting an enzyme-labeled antigen, an unlabeled antigen and an antibody to a competitive antigen-antibody reaction in a buffered solution, separating the enzyme-labeled antigen bound to the antibody from the free labeled antigen, and determining the amount of the unlabeled antigen by measuring an enzyme activity of either the labeled antigen bound to the antibody or the free labeled antigen, the improvement wherein the enzyme-labeled antigen has the following formula:

wherein X and Y are different and are each an enzyme or antigen.

15. A kit for an enzyme immuno assay which comprises subjecting an enzyme-labeled antigen, an unlabeled antigen and an antibody to a competitive antigen-antibody reaction in a buffered solution, separating the enzyme-labeled antigen bound to the antibody from the free labeled antigen, and determining the amount of the unlabeled antigen by measuring an enzyme activity of either the labeled antigen bound to the antibody or the free labeled antigen, said kit containing the following three components as essential components:

Component A: an enzyme-labeled antigen of the formula:

wherein X and Y are different and are each an enzyme or antigen,

Component B: an antibody against the antigen of component A, and

Component C: a substrate for the enzyme of the component A.

16. The kit according to claim 15, wherein the Component A is an enzyme-labeled antigen of the formula:

17. A process for preparing an enzyme-labeled antigen suitable for an enzyme immuno assay having the following formula:

wherein X and Y are different and are each an enzyme or antigen, which comprises reacting a compound of the formula:

with an antigen or enzyme containing an amino group but having no thiol group under conditions which produce a bound product of the formula:

wherein X is the same as defined above, and reacting the resulting bound product (III) with an enzyme or antigen containing a thiol group under conditions which produce the enzyme labeled antigen.

18. The process according to claim 17, wherein the compound (I) is reacted with an antigen containing an amino group but containing no thiol group, and the resulting bound product (III) is reacted with an enzyme containing a thiol group.